United States Patent
Johnson

(10) Patent No.: US 10,338,025 B2
(45) Date of Patent: Jul. 2, 2019

(54) STATIC EQUILIBRIUM PATH FOR MEASUREMENTS OF DYNAMIC FLOWS

(71) Applicant: SENTIENT TECHNOLOGIES, INC., Los Gatos, CA (US)

(72) Inventor: Frederick Quincy Johnson, Pleasanton, CA (US)

(73) Assignee: SENTIENT TECHNOLOGIES, INC, Los Gatos, CA (US)

( * ) Notice: Subject to any disclaimer, the term of this patent is extended or adjusted under 35 U.S.C. 154(b) by 0 days.

(21) Appl. No.: 16/053,528

(22) Filed: Aug. 2, 2018

(65) Prior Publication Data

US 2018/0340908 A1    Nov. 29, 2018

Related U.S. Application Data

(63) Continuation-in-part of application No. 13/625,602, filed on Sep. 24, 2012, now Pat. No. 10,060,896.

(60) Provisional application No. 61/538,050, filed on Sep. 22, 2011.

(51) Int. Cl.
*G01N 27/414* (2006.01)

(52) U.S. Cl.
CPC ....... *G01N 27/4148* (2013.01); *G01N 27/414* (2013.01)

(58) Field of Classification Search
CPC .............. G01N 33/1886; G01N 33/84; G01N 27/414–4148; A61B 2010/0032; A61B 5/14539; A61B 5/14542; A61B 5/14546; A61B 5/14507; A61B 5/4294
See application file for complete search history.

(56) References Cited

U.S. PATENT DOCUMENTS

| | | | |
|---|---|---|---|
| 4,478,222 A | * | 10/1984 | Koning .............. A61B 5/14542 600/348 |
| 5,138,251 A | | 8/1992 | Koshiishi et al. |
| 5,405,510 A | * | 4/1995 | Betts ................. A61B 5/14539 204/403.02 |
| 2005/0072672 A1 | | 4/2005 | Hoorn |
| 2007/0155037 A1 | | 7/2007 | Chou et al. |
| 2009/0026082 A1 | | 1/2009 | Rothberg et al. |
| 2010/0033188 A1 | | 2/2010 | Rieth |
| 2011/0201009 A1 | | 8/2011 | Quake et al. |

FOREIGN PATENT DOCUMENTS

WO    2009137834    11/2009

* cited by examiner

*Primary Examiner* — Maris R Kessel
(74) *Attorney, Agent, or Firm* — Fish IP Law, LLP

(57) ABSTRACT

A meter is adapted for measuring concentrations of a chemical in a flowing solution. The meter has a barrier that shields a sensor from the high turbulence of the solution flow. One or more membranes can be employed to selectively filter out various ions or other chemicals.

9 Claims, 5 Drawing Sheets

STATIC EQUILIBRIUM PATH FOR MEASUREMENTS OF DYNAMIC FLOWS

This application claims priority to U.S. application Ser. No. 13/625,602 filed Sep. 24, 2012, which claims priority to U.S. provisional application Ser. No. 61/538,050 filed Sep. 22, 2011, each of which is incorporated herein by reference in its entirety.

FIELD OF THE INVENTION

The field of the invention is measurement devices of solution flows.

BACKGROUND

Determining accurate concentration measurements in flowing solutions has long been a problem. For example, when determining the salt content of a river, one cannot simply stick a saline meter in the river. The constant flow of water would cause the saline meter to spike at some points of the measurement and dip at other points of the measurement. In order to combat this problem, a user might first pull out water from the river using a, and then dip the saline meter within the water in order to take an accurate measurement.

In fact, it is common to first remove a sample of solution from a solution flow in order to take an accurate measurement. WO2009137834 to Difoggio and US20110201009 to Quake both teach methods where a user removes a sample of solution from a turbulent flow, and then places that solution within the meter in order to obtain an accurate concentration measurement of molecules within the solution.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

US2011/0201009 to Quake teaches a method of using light in order to detect and sort biological materials and measures materials so rapidly that the speed at which the solution moves past the detection window is largely irrelevant for normal solution flow. Not all materials, however, can be detected using a light sensor. Many chemicals can only be detected by a chemical or electrical reaction with a reactive material, which requires a substantially static equilibrium in order to take accurate measurements.

Thus, there is still a need for improved systems and methods to measure the concentration of chemicals within a turbulent solution.

SUMMARY OF THE INVENTION

The inventive subject matter provides apparatus, systems and methods in which a meter that measures the concentration of a chemical in a solution provides a barrier that is constructed about the concentration gate that shields the gate from the high turbulence of the solution flow. The barrier is situated such that a relatively high turbulence portion of the solution flow has liquid access to the relatively low turbulence portion around the gate, allowing the concentration of the chemical to have a relative equilibrium of concentration with the concentration of chemical within the solution flow.

Various objects, features, aspects and advantages of the inventive subject matter will become more apparent from the following detailed description of preferred embodiments, along with the accompanying drawing figures in which like numerals represent like components.

One should appreciate that such a device could be highly useful in measuring the concentration of a chemical within a highly turbulent solution flow, such as a river or the bloodstream of a person, which constantly flows from a source to a destination. Without such a barrier, a user would need to remove a sample from the solution flow to maximize.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
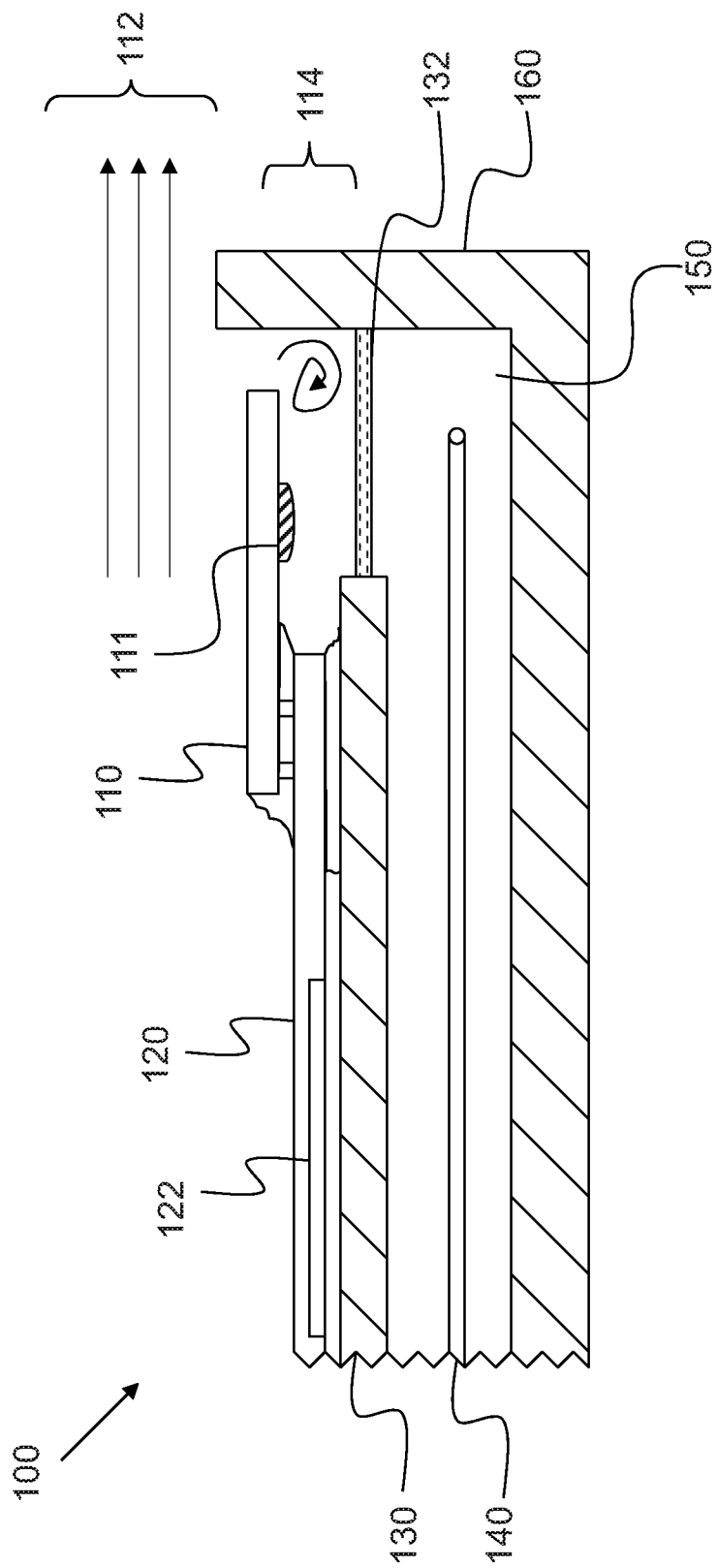
FIG. 1 is a schematic of an embodiment of the present invention.

In FIG. 1, a contemplated device 100 generally comprises a chip substrate 110 that provides a barrier between a relatively high turbulence area 112 and a relatively low turbulence area 114. As used herein, a "relatively high turbulence area" is an area where a solution being tested has a high turbulence relative to the "relatively low turbulence area." Preferably, the relatively high turbulence area 112 has liquid access to the relatively low turbulence 114 area so as to allow osmotic flow or natural diffusion of chemicals between the relatively high turbulence 112 area and the relatively low turbulence area 114.

Chip substrate 110 comprises a chip substrate for sensor 111, allowing for the chip substrate to provide dual-purpose utility as both a substrate for an ISFET sensor gate as well as the barrier between the relatively high turbulence portion of the solution being tested and the relatively low turbulence portion of the solution being tested. Chip substrate 110 is coupled to circuit board 120, which in turn is coupled to wall 130 having FRIT 132, which helps separate the reference electrode 140 and ionizing solution 150 from low turbulence area 114. Wall 160 also helps provide a barrier between the high turbulence area 112 and low turbulence area 114.

Circuit board 120 is preferably coupled to chip substrate 110 using a waterproof glue, such as polyurethane, and monitors electric activity across the sensor 111. Sensor 111 is shown here as an ISFET gate, but any other chemical concentration sensor could be used without departing from the scope of the invention. Circuit board 120 has a processor (not shown) that could then calculate the concentration of an ion within the solution being tested as a function of electric activity across the ISFET gate, such as a voltage potential across the ISFET gate or current across the ISFET gate. Since the surface of the circuit board is directly coupled to the surface of the chip substrate, a portion of the circuit board also acts as a portion of the wall housing the low turbulence area 114.

Circuit board 120 is also coupled to reference electrode 140, which is separated from the low turbulence portion 114 by frit 132. Here, the reference electrode 140 is a silver material with an AgCl coating, which interfaces with ionizing solution 150, which could vary, but is preferably a super-saturated KCl and/or AgCl solution.

Figure 2:
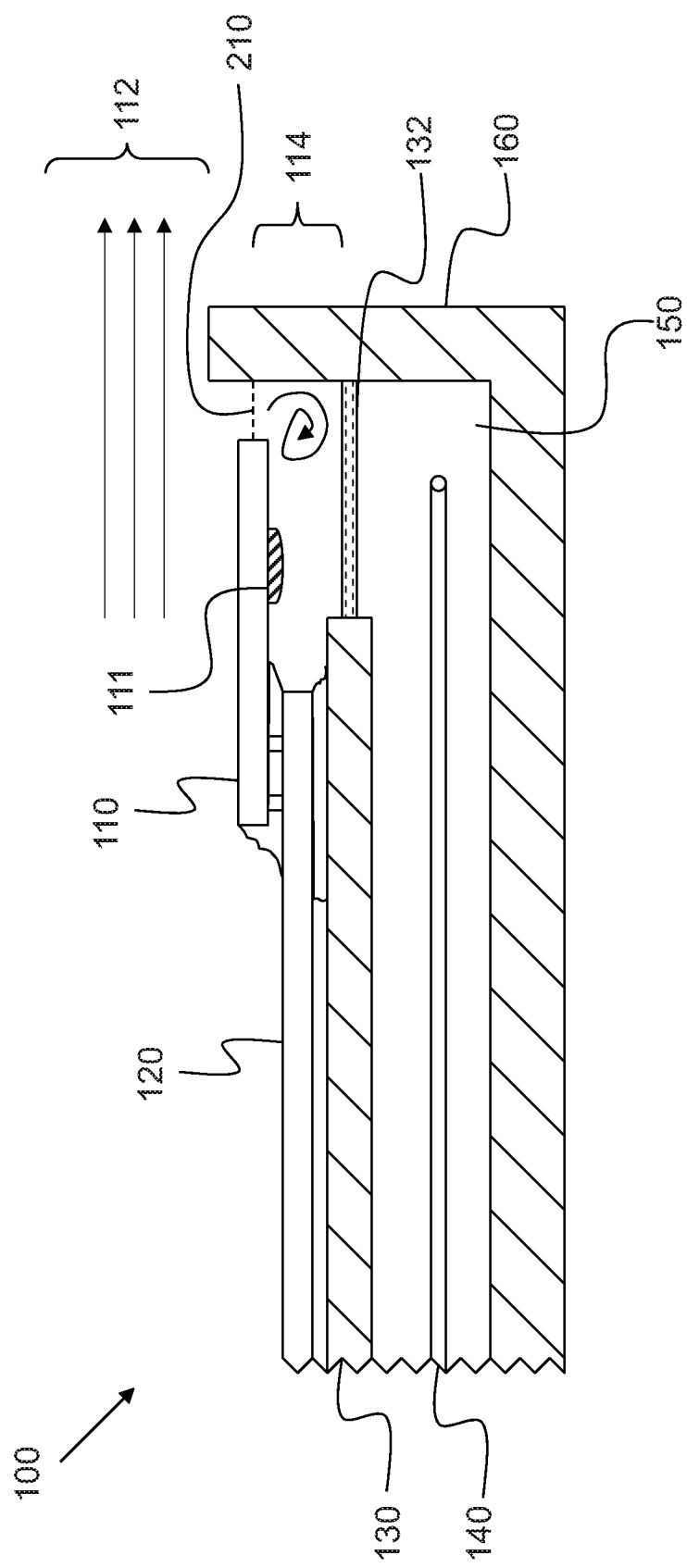
FIG. 2 is a schematic of the embodiment of FIG. 1, using a filtering membrane.

In FIG. 2, a filtering membrane 210 is positioned between the relatively high turbulence area 112 and the relatively low turbulence area 114. The filtering membrane 210 allows only a subset of chemicals to travel into the relatively low turbulence area to allow for the sensor to only test for the presence of that subset of chemicals within the solution being tested.

Contemplated high turbulence solutions include the blood stream of an animal, clean or sewage water flowing through a pipeline, or water flowing through a stream or ocean. By providing a barrier to create a "lee" around sensor 111, a low turbulence area could be provided that decreases the turbulence around the sensor by at least 4, 5, 10, 20, or 30 times in order to improve the accuracy of a concentration measurement of the solution being tested. Preferably, a width of the opening between the high turbulence area and the low turbulence area is at most a centimeter, and even more preferably is at most 5 mm or 2 mm. In the present embodiment of FIG. 1, the width of the opening between the high turbulence area and the low turbulence area is ⅓ the depth of the low turbulence area, however in the embodiment of FIG. 2, the width of the opening between the high turbulence area and the low turbulence area is ⅙ of the depth of the low turbulence area. It should be understood that the lower the ratio between the width of the opening between the high turbulence area and the low turbulence area, the longer the device needs to remain in the solution being tested in order to obtain an accurate measurement.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Figure 3:
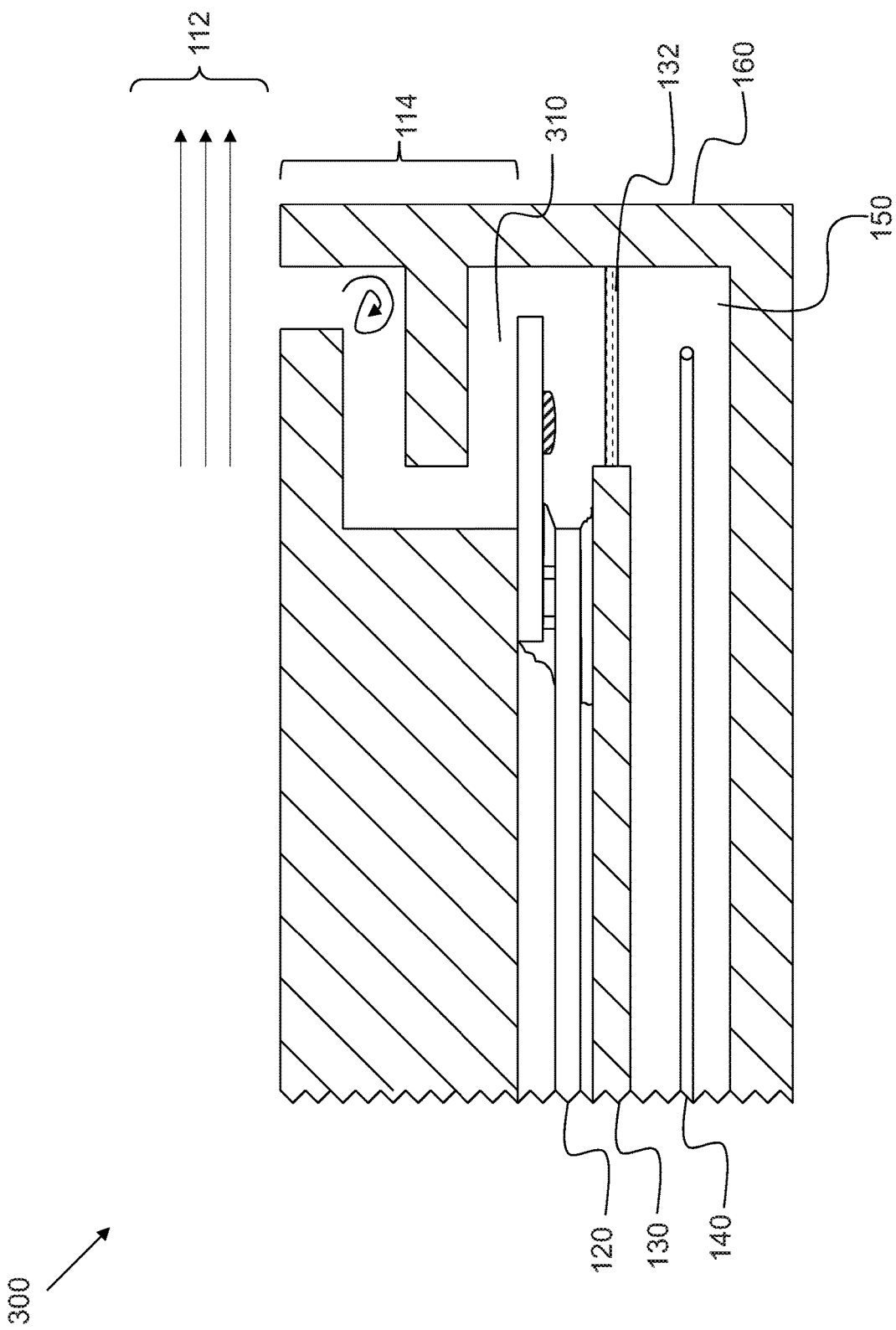
FIG. 3 is a schematic of the embodiment of FIG. 1, with multiple bends in the low turbulence area.

In FIG. 3, one or more bends 310 is positioned within the low turbulence area 114 to further decrease the amount of turbulence around the area of the sensor.

Figure 4:
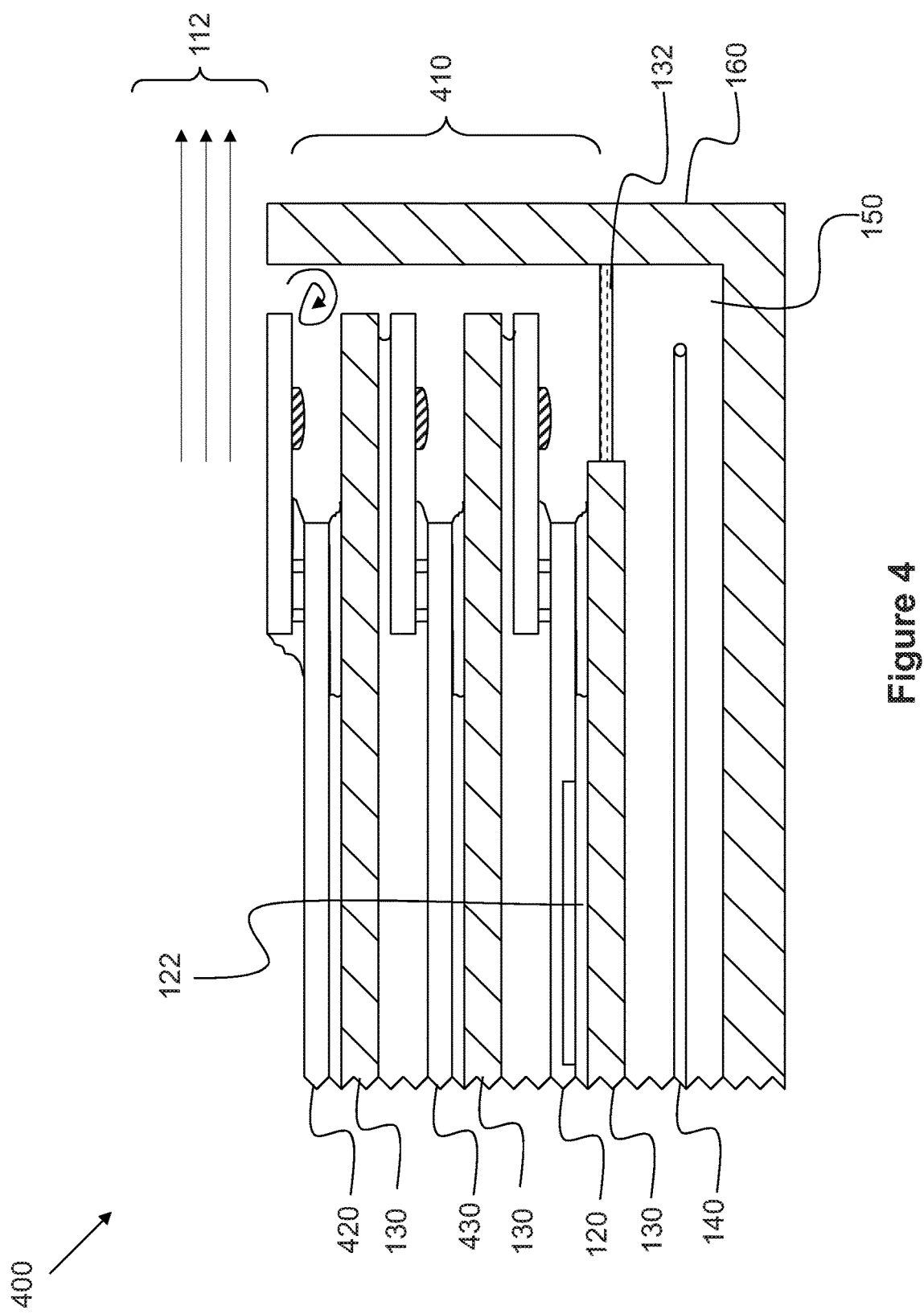
FIG. 4 is a schematic of the embodiment of FIG. 1, with multiple testing gates.

In FIG. 4, multiple "capillary" low turbulence areas 410 have been defined to allow simultaneous determination of ion concentration in each capillary channel by multiple gates, increasing the accuracy of a measurement. The two upper circuit boards 420 and 430 are functionally coupled with circuit board 120 so that processor 122 could calculate the concentration of ions within each gate area.

Figure 5:
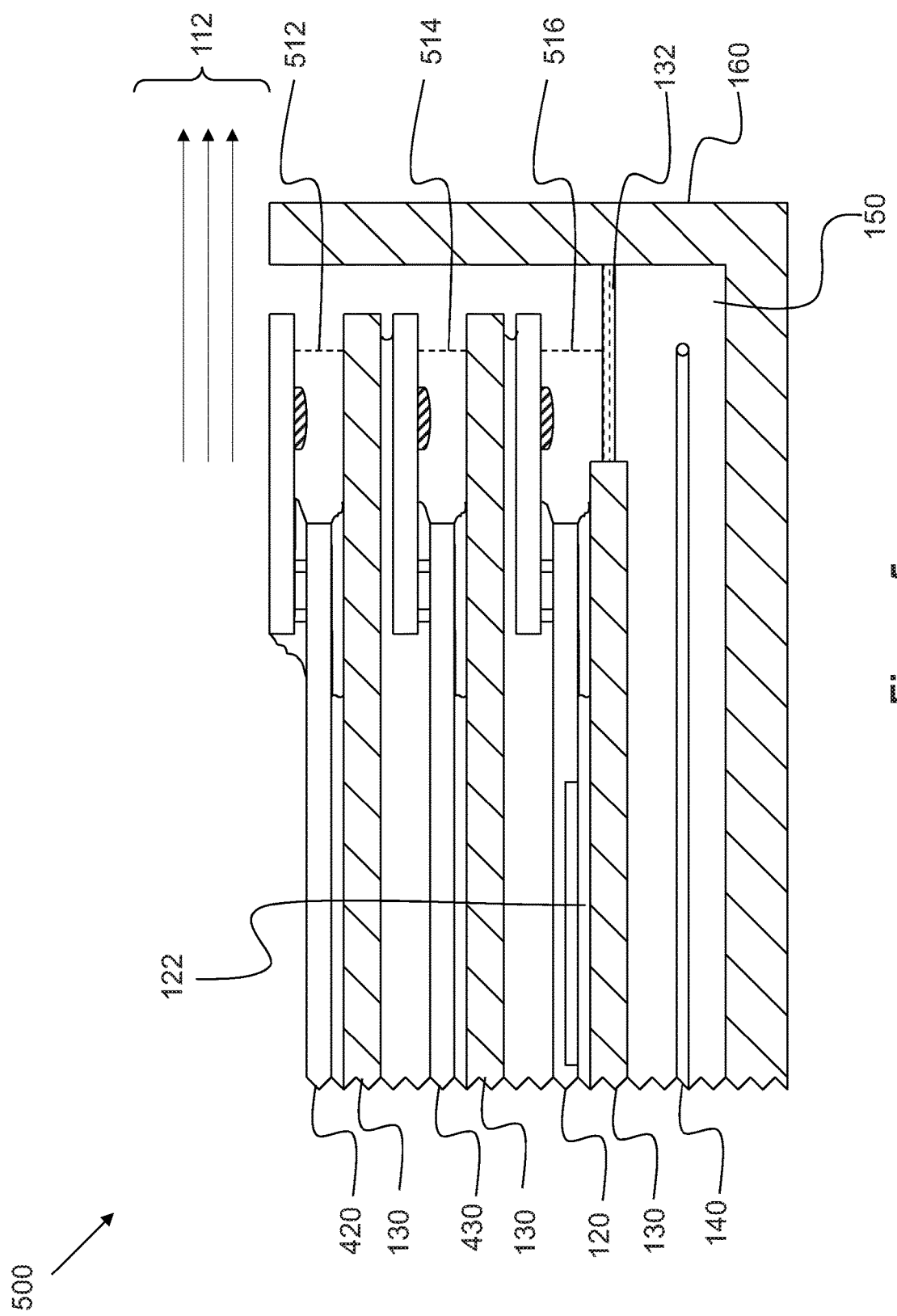
FIG. 5 is a schematic of the embodiment of FIG. 1, with multiple ion selective membranes.

In FIG. 5, multiple selective membranes 512, 514, and 516 have been provided before each capillary to allow for a wide variety of ions to be determined simultaneously using the same parent solution being tested.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An ion meter for measuring a solution with dynamic flow, comprising:
    a substrate having an interior side with an ISFET gate, and an exterior side, a reference electrode;
    a circuit board bonded to at least a portion of the substrate; and
    a barrier comprising the interior side of the substrate, the ISFET gate, and a portion of the circuit board;
    wherein the barrier partially defines a cavity providing a static equilibrium environment for the solution; and
    wherein the barrier further partially defines a fluid pathway to the exterior side of the substrate.

2. The ion meter of claim 1, wherein the substrate comprises silicon.

3. The ion meter of claim 1, wherein a liquid turbulence in the cavity is lower than a liquid turbulence on the exterior of the substrate.

4. The ion meter of claim 1, wherein the liquid turbulence in the cavity has a liquid turbulence of at most 25% the liquid turbulence at the exterior of the substrate.

5. The ion meter of claim 1, further comprising a filtering membrane spanning the fluid pathway to separate the cavity from the exterior side of the substrate.

6. The ion meter of claim 5, wherein the filtering membrane selectively prevents at least one solute from entering the cavity.

7. The ion meter of claim 1, wherein the fluid pathway to the exterior side of the substrate comprises at least one switchback bend.

8. The ion meter of claim 1, further comprising a frit layer in direct communication with the cavity, wherein the frit layer fluidly separates the reference electrode from the cavity.

9. The ion meter of claim 8, wherein the frit layer fluidly seals the reference electrode in a chamber containing ionizing solution.

* * * * *